United States Patent [19]

Beachey

[11] Patent Number: 4,705,684
[45] Date of Patent: Nov. 10, 1987

[54] SYNTHETIC M PROTEINS - STREPTOCOCCI TYPE 6

[75] Inventor: Edwin H. Beachey, Memphis, Tenn.

[73] Assignee: The University of Tennessee Research Corporation, Knoxville, Tenn.

[21] Appl. No.: 839,750

[22] Filed: Mar. 14, 1986

Related U.S. Application Data

[63] Continuation-in-part of Ser. No. 739,963, May 31, 1985, abandoned.

[51] Int. Cl.[4] ........................ A61K 37/02; C07K 7/06; C07K 7/08; C07K 7/10

[52] U.S. Cl. .................................... 424/88; 530/326; 530/327; 530/328

[58] Field of Search .................... 514/14, 15; 530/326, 530/327, 328; 424/88

[56] References Cited

U.S. PATENT DOCUMENTS 4,597,967 7/1986 Beachey .............................. 530/324

Primary Examiner—Delbert R. Phillips
Attorney, Agent, or Firm—Weiser & Stapler

[57] ABSTRACT

Synthetic immunogenic peptides when linked to a suitable carrier elicit opsonic antibodies which are type specific for type IV streptococci are disclosed.

21 Claims, 1 Drawing Figure

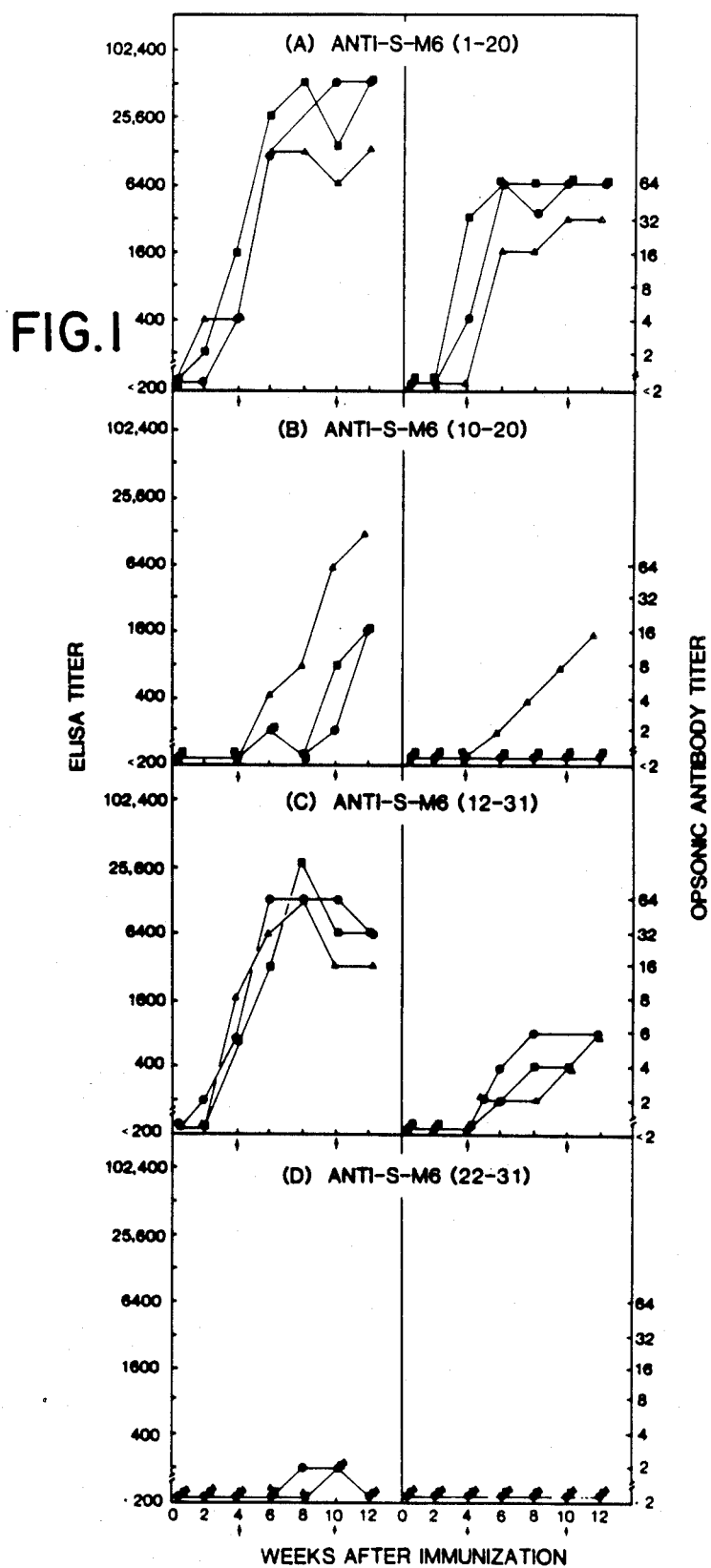

SYNTHETIC M PROTEINS - STREPTOCOCCI TYPE 6

This application is a continuation-in-part of U.S. application Ser. No. 739,963 entitled Biologically Active Hybrid Peptides of Streptococcal M Protein and Compositions and Use, filed May 31, 1985, abandoned wherein Edwin H. Beachey, Andre Tartar, Helene Gras-Masse, Michel Jolivet, Francoise Audibert and Louis Chedid are named inventors.

This invention relates to peptide fragments of the M protein of *S. pyogenes*. More particularly, the invention relates to synthetic immunogenic peptides which, when linked to a suitable carrier, elicit opsonic antibodies which are type-specific for type 6 streptococci and which are not serologically cross-reactive with tissue antigens of the human or the host heart.

The invention further relates to the synthetic antigen conjugates of these haptens with appropriate carriers which evoke immune responses which are type specific for type 6 streptococci, and which are not serologically cross-reactive with tissue antigens of the human or host heart.

The invention further relates to the biologically active compositions which comprise the synthetic antigen conjugates and a biologically acceptable diluent and which are immunogenic with respect to *Streptococcus pyogenes*.

The invention further relates to vaccines which comprise the synthetic antigen conjugates which are effective to immunize a patient against type 6M protein of *Streptococcus pyrogenes*.

The invention further relates to the method for controlling streptococcal infections in a mammal which comprises administering the biologically active compositions to said mammal.

For over one-half century, attempts have been made to develop safe and effective vaccines against strains of group A streptococci that give rise to rheumatic fever and rheumatic heart disease (Lancefield, R. C., J. Immunol., 89, 307 (1962) and Stollerman, G. H., *Rheumatic Fever and Streptococcal Infection,* Grune and Stra Hon, New York, 1975). Most of these efforts have been frustrated by severe toxic reactions to almost any streptococcal product introduced into the human host. Some of these products have been shown to give rise to antibodies that cross react with host tissues, especially the heart (Kaplan, M. H. and Meyersian, H., Lancet, I., 706 (1962) and Zabriskie, J. B. and Freimer, E. H., J., Esp. Med., 124, 661 (1966)). Although it has long been established that the M protein on the surface of group A streptococci contains the protective antigen(s) of these organisms, the fear has been that the isolated M protein may be associated with potentially harmful tissue cross-reactive antigens that give rise to, rather than prevent, rheumatic fever. This fear has been perpetuated by the finding that certain rheumatogenic streptococci produce M proteins that are closely associated with a heart cross-reactive antigen (Kaplan, M. H., J. Immunol., 90, 595 (1963)). Indeed recently it has been established that one of the M protein molecules contains, within its covalent structure, an epitope that elicits a protective anti-streptococcal antibody that also cross-reacts with a sarcolemmal protein of human heart tissue (Dale, J. B. and Beachey, E. H., J, Exp. Med., 156, 1165 (1982)).

Recently Audibert et al. actively immunized laboratory animals against diphtheria toxin used a chemically synthesized oligopeptide (Audibert, F. et al., Nature 289, 593–594 (1981)). This work does not show, however, that a synthetic peptide antigen can raise antibodies which promote phagocytosis and killing of a bacterial pathogen.

U.S. Pat. No. 4,284,537, to E. Beachey, issued Aug. 18, 1981, disclosed the amino acid sequence of two peptide fragments derived from type 24M protein. It also disclosed that each of these natural fragments, when covalently linked to a carrier such as polylysine, was able to elicit type-specific opsonic antibodies effective against *Streptococcus pyogenes*. Each of these fragments was a natural extract, and each contained 35 amino acids.

The above-referred to U.S. Pat. No. 4,284,537 describes inter alia, a synthetic peptide (S-CB7) and that one of the protective determinants is located in a specific fragment of S-CB7 of type 24M protein which contains only twelve amino acid residues (S-CM7(18–29)). S-CB7, as described, differs from the native CB-7 fragment in that the COOH-terminal residue of S-CB7 is methionine, in contrast to homoserine. The specification also teaches and described covalently linked conjugates of S-CB7 and appropriate hapten carriers, natural, like BSA or OVA or synthetic, like polylysine. Further details about his work have been published in Nature on July 30, 1981, by Beachey et al, 292, pages 457–459.

U.S. Pat. No. 4,521,334, entitled Synthetic Polypeptide Fragments, to Edwin H. Beachey, issued June 4, 1985, discloses the amino acid sequence of three peptide fragments CB3, CB4, and CB5, and 35 and 37 amino acid sequences of type 24M which contain antigenic determinants corresponding to the antigenic determinants contained in CB3–CB7. It also discloses that these fragments, when covalently linked to a carrier such as polylysine, are able to elicit type-specific opsonic antibodies effective against *Streptococcus pyogenes*.

U.S. application Ser. No. 739,963 entitled "Biologically Active Hybrid Peptides of Streptococcal M Protein and Compositions and use" to Edwin H. Beachey et al filed May 31, 1985 disclosed peptide sequences containing fragments of M5, M6, and M24 proteins which are able to elicit opsonic and bactericidal antibodies to *Streptococcus pyogenes* which are not serologically cross-reactive with tissue antigens of the human or host heart. The only fragment of Type 6M protein disclosed is S-M6(1-11).

Notwithstanding these advances, there remains a serious need, as yet unfilled, to identify and synthesize protective regions of other rheumatogenic serotypes so that a combination of protective peptides could be incorporated into a single vaccine to evoke protective immunity against many rheumatogenic serotypes of group A streptococci without causing tissue cross-reactive adverse reactions. The problem has been described by Hasty et al, in the J. Exp. Med., Vol. 155, page 1010, April 1982. Another attempt in predicting protein antigenic determinants from amino acid sequences (including the streptococcal M protein) has been published by Hopp et al in the Proc. Natl. Acad. Sci. USA, Vol. 78, No. 6, pages 3824–28, June 1981. The present invention marks another forward step and provides another advance in the medical sciences, particularly in the control of streptococcal infections.

Accordingly, it is a primary object of the invention to provide peptide fragments which are useful as haptens which when linked to a suitable carrier are able to inhibit opsonic antibodies obtained from a mammal which has been immunized with uncleaved pep M 6 molecules.

Another object of the invention is the production of biologically active compositions which are immunogenic with respect to *S. pyogenes*.

Another object of the invention is to provide for a method of controlling type 6M streptococcal infections in a mammal.

Other worthwhile objects will become apparent from the disclosure herein. Other features and advantages of the invention will appear from the examples which follow and by referring to the appended drawing in which:

FIG. 1 shows immune responses of rabbits against chemically synthesized peptide fragments of type 6 streptococcal M protein conjugated to tetanus toxoid as measured by ELISA against pep M 6 (left) and opsonic antibody assays against type 6 streptococci (right). Sets of three rabbits (●, □, △) were injected s.c. with 25 nmol of tetanus toxoid conjugated S-M6(1–20)(Panel A), S-M6(10–20)(Panel B), S-M6(12–31)(Panel C), or S-M6(22–31)(Panel D) emulsified in CFA. Booster injections of 25 nmol of the respective peptide conjugates in PBS were given at 4 and 10 wk as indicated by the arrows. In control experiments, none of the immune sera opsonized heterologous M serotypes 5, 19, and 24 streptococci, although some of the sera cross-reacted weakly with the heterologous types of pep M protein by ELISA (see Table III).

The mechanism whereby streptococcal infections give rise to complications such as rheumatic fever have remained, to a large extent, unexplained to date. Because the sera of some patients with rheumatic fever show serological cross-reactivity between heart tissue antigens and certain streptococcal antigens, it has been feared that immunization with intact M-protein vaccines may lead to rheumatic heart disease. See, for instance, Stollerman, *Rheumatic Fever and Streptococcal Infection*, supra. It has been observed that rabbits and mice immunized with cyanogen bromide fragments (CB6 or CB7) of type 24M protein containing only 35 amino acid residues each developed opsonic and protective antibodies against type 24 streptococci.

Recently, it has been demonstrated that serotypes 5, 6, and 19M proteins share antigenic determinants with human sarcolemmal membranes (Dale, J. B. and E. H. Beachey, 1982, J. Exp. Med. 156:11654; Dale, J. B. and E. H. Beachey, 1982, Trans. Assoc. Am. Physicians 95:286; Dale, J. B. and E. H. Beachey, 1985, J. Exp. Med. 161:113) as well as with cardiac myosin (Dale, J. B. and E. H. Beachey, 1985, J. Exp. Med. 162:583). Because the M protein contains the only protective antigenic determinants of virulent group A streptococci (Lancefield, R. C., 1962, J. Immunol. 89:307), it has become imperative to carefully identify the regions of the molecule that contained protective as opposed to cardiac tissue cross-reactive epitopes. The notion that one may be able to evoke protective immunity with peptide fragments of various regions of the M protein molecule was first suggested by studies of the protective immunogenicity of large polypeptide fragments extracted by limited digestion of streptococcal cells with dilute solutions of pepsin at pH 5.8 (Beachey, E. H., G. L. Campbell, and I. Ofek, 1974, Infect. Immun. 9:891; Beachey, E. H., G. H. Stollerman, E. Y. Chiang, T. J. Chiang, J. M. Seyer and A. H. Kang, 1977, J. Exp. Med. 145:1469; Manjula, B. N. and V. A. Fischetti, 1980, J. Immunol. 124:261; Seyer, J. J., A. H. Kang and E. H. Beachey, 1980, Biochem. Biophys. Res. Commun. 92:546). These fragments, ranging in $M_r$ from 19,000 to 33,500, were shown to be highly immunogenic, stimulating protective antibodies against the related streptococci in laboratory animals (Beachey, Infect. Immunity, J. Exp. Med., Ibid.), as well as in humans (Cunningham, M. and E. H. Beachey, 1975, J. Immunol. 115:1002). Subsequent studies of yet smaller fragments derived from type 24M protein by cyanogen bromide cleavage demonstrated that the five repeating 35-residue fragments, as well as 90-residue fragment each contained protective epitopes, and when covalently linked to polylysine had the capacity to evoke type-specific protective immunity against type 24 streptococci (Beachey, E. H., J. M. Seyer, and A. H. Kang, 1980, J. Biol. Chem. 255:6284; Beachey, E. H., J. M. Seyer, J. B. Dale, and D. L. Hasty, 1983, J. Biol. Chem. 258:13250; Beachey, E. H., J. M. Seyer and A. H. Kang, 1978, Proc. Natl. Acad. Sci. USA 75:3163) Moreover, chemically synthesized copies of the 35-residue fragments 3 and 7 (S-CB3 and S-CB7, respectively), as well as subpeptide fragments of S-CB7 containing as few as 13 amino acid residues of type 24M protein had the capacity, when linked to a carrier, to evoke type-specific protective immunity (Beachey, E. H., J. M. Seyer, J. B. Dale, W. A. Simpson and A. H. Kang, 1981, Nature 292:457; Beachey, E. H., J. M. Seyer, J. B. Dale and D. L. Hasty, 1983, J. Biol. Chem. 258:13250; Beachey, E. H., A. Tartar, J. M. Seyer, and L. Chedid, 1984, Proc. Natl. Acad. Sci USA 81:2203).

Having established the principle of the protective immunogenicity of small peptide fragments of the repeating covalent structure of type 24M protein, a serotype of which the pepsin-extracted polypeptide fragment is devoid of tissue cross-reactive antigens, studies have turned to the serotypes of M proteins shown to contain such cross-reactive determinants. It has been shown that a chemically synthesized peptide copy of the first 20 residues of the $NH_2$-terminus of type 5M protein evoked type-specific protective antibodies in rabbits without stimulating heart cross-reactive antibodies (Dale, J. B., J. M. Seyer, and E. H. Beachey, 1983, J. Exp. Med. 158:1727).

In accordance with the present invention overlapping peptides copying the $NH_2$-terminal region of type 6M protein have been synthesized. Type 6M serotype has been shown to contain cardiac tissue cross-rective epitopes (Dale, J. Exp. Med. 161, op.cit). Several of the peptides have been found to be immunogenic with respect to *S. pyogenes*.

As non-limiting examples of this invention, there were prepared synthetic peptides of M6. Some of the peptides are designated by the general formula

X-Lys-Ala-Arg-Glu-Leu-Leu-Asn-Y wherein

X is Asp, Asn-Pro-Asp or

Arg-Val-Phe-Pro-Arg-Gly-Thr-Val-Glu-Asn-Pro-Asp and

Y is Lys or

Lys-Tyr-Asp-Val-Glu-Asn-Ser-Met-Leu-Gln-Ala-Asn. Within the general formula, the synthetic peptides include those labeled as S-M6(1–20), S-M6(10–20), S-M6(12–31) and S-M6(22–31).

The amino acid sequences of the synthetic peptides S-M6(1–20) is Arg-Val-Phe-Pro-Arg-Gly-Thr-Val-Glu-Asn-Pro-Asp-Lys-Ala-Arg-Glu-Leu-Leu-Asn-Lys.

The amino acid sequence of S-M6(10–20) is Asn-Pro-Asp-Lys-Ala-Arg-Glu-Leu-Leu-Asn-Lys.

The amino acid sequence of S-M6(12–31) is Asp-Lys-Ala-Arg-Glu-Leu-Leu-Asn-Lys-Tyr-Asp-Val-Glu-Asn-Ser-Met-Leu-Gln-Ala-Asn.

The amino acid sequence of S-M6(22–31) is Asp-Val-Glu-Asn-Ser-Met-Leu-Gln-Ala-Asn.

The structures of the peptides are also shown in Table I in single letter code (IUPAC-IBU Commission on Biochemical Nomendatures (1968) J. Biol. Chem. 243, 3557-3559) for ease of comparison.

The synthetic peptides of the invention also include the peptide labeled as S-M6(1–11).

The amino acid sequence of S-M6(1–11) is Arg-Val-Phe-Pro-Arg-Gly-Thr-Val-Glu-Asn-Pro.

Other amino acid sequences of type 6M protein having ability to elicit opsonic antibodies to type 6M protein when conjugated to a carrier are also within the scope of the invention.

It is also within the scope of the invention that certain amino acids within the peptide sequences be substituted by other amino acids. The resulting sequences have equivalent ability to elicit opsonic antibodies to type 6M protein.

In accordance with the invention the synthetic peptides were conjugated with a covalently linkable carrier. Four of the conjugates proved to be capable of producing immune responses against M6 as measured by opsonic antibody and ELISA tests. When covalently linked with glutaraldehyde to tetanus toxoid three of the conjugates (S-M6(10–20), S-M6(12–31) and S-M6(1–20)) evoked opsonic and protective antibodies in rabbits. When covalently linked to KLH, the conjugate of S-M6(1–11) evoke opsonic antibodies in rabbits.

Furthermore, none of the conjugates synthetic peptides raised antibodies that were cross-reactive with human heart tissue.

In accordance with the invention, the carriers which are used to make the conjugate with the peptide sequences of the invention are any "natural" or synthetic carrier. The term carrier is a recognized term in the art and literature and sometimes is referred to as "coupler" or as "protein carrier". Numerous molecules, especially proteins and polysaccharides (in the mouse), may be coupled covalently to a hapten to act as a carrier. For this purpose, haptens may also be bound to erythrocytes, bacteriophages, artificial or synthetic macromolecules, and even to insoluble carriers. The hapten should possess one or several reactive groups that permit binding (covalent bonds) to carrier functional groups, under physiochemical conditions that maintain the integrity of the hapten structure, and as much as possible, of the carrier protein.

In some cases, binding of hapten to carrier requires mere contact (this is the case for nitrophenyl derivatives); most often, however, a coupling agent is required. When the hapten itself does not possess any reactive group, it may be introduced through a previous reaction. Thus, in order to couple steroids without carboxyl function to proteins, their alcohol function may be transformed into hemisuccinate, which introduces a carboxyl group.

Natural carriers used in accordance with the invention are known and are, typically, tetanus toxoid, keyhole limpet hemocyanin (KLH), BSA or OVA. Synthetic carriers are, typically, polylysine. Hapten carriers as well known in the literature and need not be further described here to one skilled in the art. Generally, these carriers are covalently linked to the protein sequence.

Moreover, it has been found that the coupled antigen can be administered with a natural immunostimulant, preferably of the MDP type, like MDP, its analogs and derivatives in aqueous saline solution, such as phosphate buffered saline ("PBS").

It is contemplated in accordance with the invention that whenever the term "MDP" is used for the synthetic immunostimulant, the term is and does include any synthetic immunostimulant which contains (or encompasses, or includes, etc.) the basic MDP (or the nor-MDP, i.e., 2-(2-acetamido-2-deoxy-D-glucose-3-O-yl-D-propionyl-L-alanyl-D-isoglutamine), structure, which structure has been recognized in the art to be the minimal structure to contribute to immunogenicity. The term "MDP immunostimulant", or "MDP type" or "nor-MDP type" or MDP analogs and derivatives are to be taken broadly. Such MDP immunostimulants are well known in the literature, which is incorporated by reference and include the following for illustrative purposes. U.S. Pat. Nos. 4,082,735; 4,082,736; 4,153,684; 4,220,637; 4,101,649; 4,186,194; 4,235,771; and the following publications: *Biken Journal*, Vol. 18, 105–111, 1975; *Microbiology* (1977) 388–394; *Cellular Immunology* 21, 243–249 (1976); *Proc. Natl. Acad. Sci. USA*, Vol. 73, No. 7, pps. 2472–2475, July 1976; *Int. J. Peptide Protein Res.*, 9, 1977, pps. 249–257; *Biken Journal*, Vol. 20, pps. 95–103, 1977; *C. R. Acad. Sci. Paris*, t. 285 (12 Sept. 1977); *Prog. Allergy*, Vol. 25, pps. 63–105 (Karger, Basel 1978); and *Cellular Immunology* 35, pps. 173–179 (1978).

When covalently linked to tetanus toxoid, the synthetic peptides, S-M6(1–20), S-M6(10–20), and S-M6(12–31), but not S-M6(22–31) evoked opsonic antibodies in rabbits against type 6 streptococci. Although the antisera raised against S-M6(22–31) failed to opsonize type 6 streptococci or react with pep M6 by ELISA, the antisera each reacted in high titer with S-M6(22–31), the immunizing antigen, as well as with S-M6(12–31) of which the former peptide is a part. Thus, the antibodies raised against the 22–31 peptide were directed against antigenic determinants not accessible in the natural M protein molecule, and therefore were nonprotective.

When covalently linked to KLH, the synthetic peptide S-M6(1–11) evoked opsonic antibodies in rabbits against type 6 streptococci.

The sequences of the synthetic peptides S-M6(1–20), S-M6(12–31), S-M6(10–20), and S-M6(22–31) were confirmed by automated Edman degradation (Table I). They were found to be identical to the corresponding regions of pep M6, according to the amino acid sequence published by Manjula and Fischetti (1980), J. Exp. Med. 151:695; Fischetti et al (1983), J. Exp. Med. 159:1083; and Scott et al (1985), Proc. Natl. Acad. Sci USA 82:1822.

To determine whether or not the synthetic peptides contained immunodominant epitopes of the type 6M protein molecule, the reactivity of each of the peptides with sera from rabbits immunized with whole type 6 streptococci was investigated. The immune sera of two rabbits immunized with whole type 6 streptococci reacted at high dilutions with pep M6, S-M6(1–20), and S-M6(10–20), and at low dilutions with S-M6(12–31) and S-M6(22–31) (Table II). These results suggested that the NH$_2$-terminus of the type 6M protein molecule contains major immunogenic determinants of the native M protein exposed on the surface of type 6 streptococci.

The conjugated peptides S-M6(1-20), S-M6(10-20), S-M6(12-31) and S-M6(22-31) were emulsified in CFA and were injected in 100 ug doses (of peptide) into the skin of each of three rabbits. Booster injections of the same dose of the respective peptides dissolved in PBS alone were given s.c. at 4 and 10 wk after the initial injection. Each of the synthetic peptides except S-M6(22-31) evoked high titers and antibody against the purified pep M6 molecule in each of the immunized rabbits as measured by ELISA (FIG. 1). The immune sera of each of the rabbits immunized with S-M6(1-20) or S-M6(12-31), and one of three rabbits immunized with S-M6(10-20) opsonized type 6 streptococci, whereas none of the sera from animals immunized with S-M6(22-31) was opsonic (FIG. 1).

To confirm the protective activity of the antisera that opsonized the type 6 streptococci, indirect bactericidal tests were performed (Table III). Each of the opsonic antisera reduced the survival of type 6 streptococci rotated with fresh human blood; the antiserum from rabbit 8413 against S-M6(1-20) and from rabbit 8416 against S-M6(12-31) completely sterilized the test mixtures inoculated with 34 colony-forming units of type 6 streptococci (Table III).

Although the antisera raised against each of the synthetic peptides cross-reacted weakly with heterologous serotypes of M protein by ELISA (Table IV), none of the sera opsonized the related types 5, 19, and 24 streptococci. None of the immune sera reacted with frozen sections of cardiac tissues or isolated sarcolemmal membranes in tests of immunofluorescene, or with muscle myosin by ELISA.

To determine the distribution of protective epitopes among the different synthetic peptides, the cross-reactivity of each of the immune sera with the synthetic peptides S-M6(1-20), S-M6(10-20), S-M6(12-31) and S-M6(22-31) of type 6M protein was examined. As can be seen in Table V, each of the antisera reacted strongly with the immunizing peptides, but also reacted with the other peptides to varying degrees. All except the antisera against S-M6(22-31) also recognized the natural protein pep M6. Although S-M6(22-31) failed to evoke antibodies reactive with pep M6 or opsonic antibodies against type 6 streptococci (see FIG. 1), it evoked high titers of ELISA antibody against itself, as well as against S-M6(12-31) of which it is a part (Table V). Conversely, each of the opsonic antisera aginst S-M6(12-31) reacted strongly with the immunizing peptide but very weakly with the related S-M6(22-31). The opsonic antisera against S-M6(1-20) and S-M6(10-20) also reacted strongly with these two related peptides but not at all with the overlapping S-M6(12-31). Surprisingly, one of the antisera against S-M6(1-20) reacted at a dilution of 1/3200 with S-M6(22-31), which does not overlap at all with the immunizing peptide. It should be noted, however, that the three residue sequence valine, glutamic acid, asparagine at position 8-10 is repeated at position 23-25 (see Table I).

In an attempt to determine the functional significance of the immunologic cross-reactivities among the synthetic peptides, the inhibition of opsonization by the antisera from rabbits 8413, 8416, and 8429 by each of the peptides was tested. In each case, the homologous peptide and pep M6 were the most highly inhibitory (Table VI). S-M6(22-31) failed to inhibit the opsonization by any of the antisera tested. Because of the pattern of inhibition, these results suggest the presence of at least three opsonogenic epitopes in the NH$_2$-terminal region of type 6M protein. They additionally suggest that peptide 22-31 lacks protective epitopes and its nonprotective epitopes are not present or are not accessible on the uncleaved pep M6 molecule nor on the surface of intact type 6 streptococci.

The pattern of the inhibition of opsonization (see Table IV) of the synthetic peptides of each of the immune sera indicate the presence of at least three protective epitopes in the NH$_2$-terminal region of type 6M protein; the antisera against S-M6(1-20) was inhibited only by S-M6(1-20); that against S-M6(10-20) was completely inhibited by S-M6(1-20) and S-M6(10-20) but only partially by S-M6(12-31); that against S-M6(12-31) was inhibited only by S-M6(12-31). In addition, each of the antisera was inhibited completely by pep M6 but not at all by S-M6(22-31). Thus, the synthetic peptides of the NH$_2$-terminal region of the type 6M protein molecule contain several type-specific protective and nonprotective epitopes.

The conjugated peptide S-M6(1-11) also was immunogenic and produced opsonic antibodies. It was injected into the skin of each of three rabbits. At four weeks after injection antibody against pep M6 was measured by ELISA. The precent inhibition of opsonization was also measured at four weeks. The results are shown in Table VII.

The nonprotective peptide (S-M6(12-31)) resides in the NH$_2$-terminal region of the type 6M protein in a position similar to the nonprotective peptide S-M5(20-40) of type 5M protein (Dale et al., J. Exp. Med., 1983, op. cit.). It is possible that the greater rigidity conferred on this part of the molecule by its higher α-helical potential (Manjula et al, 1980, J. Exp. Med. 151:695) and coiled-coil structure (Phillips et al., 1981, Proc. Natl. Acad. Sci. USA 78:4689) renders it less accessible to antibodies prepared against synthetic copies of this region. Manjula and Fischetti (op. cit.) pointed out that the α-helical potential of types 5, 6, and 24M proteins begins at residues 17 or 18. The seven-residue periodicity dictating an α-helix is especially pronounced between residues 27 and 54 of type 5M protein (Manjula et al., 1984, J. Biol. Chem. 259:3686) and residues 28 and 55 of type 6M protein (Scott et al., 1985, Proc. Natl. Acad. Sci. USA 82:1822). The seven-residue sequence Leu-Lys-Thr-Glu-Asn-Glu-Gly is repeated tandemly four times (residues 27-33, 33-40, 41-47, and 48-54) with a single Lys/Glu substitution at position 30 in type 5M protein (Manjula et al., J. Biol. Chem. 1984, op. cit.). A similar seven-residue peptide is tandemly repeated four times (residues 28-34, 35-41, 42-48, and 49-55) in type 6M protein (Scott et al, PNAS 1985, op. cit.), although not with the same degree of identity as that noted in type 5M protein. Nevertheless, the high degree of α-helicity in the molecular region from which the synthetic peptide S-M6(22-31) was copied theoretically should render this part of the molecule less mobile and therefore less adaptable to the many different conformations required to interact with the repertoire of antibodies raised against the more flexible synthetic peptide (Tainer et al, Nature, 1984, 312:127).

Other advantageous characteristics of the invention will appear from the non-limiting examples which follow and with reference to FIG. 1 illustrating the properties of the compounds of the invention.

EXAMPLE 1

Preparation of Streptococcal M Protein Peptides

Polypeptide fragments of M protein were isolated and purified from limited peptic digests of whole type 5, type 6, type 19 and type 24 Streptococcus pyogenes as previously described. (Beachey, et al., Infect. Immun., 9, 891 (1974); Beachey et al., J. Exp. Med., 145, 1469 (1977); Beachey et al., Proc. Natl. Acad. Sci. USA, 75, 3613 (1978)). The purified polypeptides designated pep M5, Pep M6, pep M19 and pep M24 were judged to be pure by sodium dodecyl-sulfate-gel electrophoresis and quantitative amino acid analysis.

Several overlapping peptide copies of the $NH_2$-terminal region of type 6M protein according to the amino acid sequence reported by Manjula and Fischetti et al., J. Exp. Med. 159:1083, 1983, were synthesized by the solid-phase method of Merrified, 1963, J. Am. Chem. Soc. 85:2149, as described (Beachey et al, 1984, Proc. Natl. Acad. Sci. USA, 81:2203). The synthetic peptides were purified by gel filtration on columns of Sephadex G50 and were additionally purified by reverse-phase high pressure liquid chromatography on Ultrasphere ODS2 (Whatman) (IBID). The purified peptides were analyzed for purity and composition by quantitative amino acid and automated Edman degradation to the penultimate amino acid residue (Beachey et al, 1980, J. Biol. Chem. 255:6284 and Beachey et al, 1983, J. Biol. Chem. 258:13250). In this way, the overlapping peptides together encompassing the first 31 residues of the type 6M protein molecule were synthesized; they are designated S-M6(1–11), S-M6(1–20), S-M6(10–20), S-M6(12–31), and S-M6(22–31).

EXAMPLE 2

Conjugation of Synthetic peptides with Tetanus Toxoid

The synthetic peptides were conjugated to lysylated tetanus toxoid as described (Beachey et al, 1984, Proc. Natl. Acad. Sci. USA 81:2203 and Dale et al, 1983, J. Exp. Med. 158:1727). The conjugated peptides were stored frozen in 0.02M phosphate/0.15M Nacl. pH 7.4 (PBS) at −70° C.

EXAMPLE 3

Immunization of Rabbits

To determine the immunogenicity of the synthetic peptides, New Zealand white rabbits (2 kg) were injected subcutaneously with 25 nmol dose of the respective synthetic peptide conjugated to tetanus toxoid or KLH and were emulsified in complete Freund's adjuvant as described in Beachey et al, 1984, Proc. Natl. Acad. Sci. USA 81:2203 and Dale et al, 1983, J. Exp. Med. 158:1727. Rabbits were bled immediately before the primary immunizing injection and at 2-week intervals thereafter. At four and ten weeks, each rabbit was injected s.c. with a 25 nmol booster dose of the same peptide in phosphate-buffered saline (PBS; 0.02M phosphate/0.15M NaCl, pH 7.4). Antisera against pep M5, pep M6, pep M19, and pep M24 were prepared by immunizing rabbits with 3 nmol doses of the respective pep M proteins emulsified in CFA (Beachey et al, 1977, J. Exp. Med. 145:1469), and against whole type 6 streptococci by injecting rabbits intracutaneously with a 1-ml PBS suspension of $10^9$ streptococcal units (heat-killed at 56° C. for 30 min) followed by i.p. and i.v. booster injections of the same dose of bacteria (Cunningham et al, 1975, J. Immunol. 115:1002). All sera were stored at 4° C.

EXAMPLE 4

Assays for Anti-M Protein Antibodies in Rabbit sera

The rabbit sera were assayed for anti-M protein antibodies against M protein by enzyme-linked immunosorbent assays (ELISA), opsonophagocytic assays and indirect bactericidal assays as described (Beachey et al, 1979, J. Exp. Med. 150:862). The serotype specificity of the antibodies to the synthetic peptide copies of type 6M protein was determined by assaying the antisera against pep M5, pep M6, pep M19, and pep M24 by ELISA and against live types 5, 6, 19, and 24 streptococci in opsonophagocytic assays (Beachey et al, 1979, J. Exp. Med. 150:862).

EXAMPLE 5

Assays for heart cross-reactive antibodies

Each of the rabbit antisera was examined for immunologic cross-reactivity with human cardiac sarcolemmal membrances as described (Dale et al, 1982, J. Exp. Med. 156:11654). In addition, they were assayed for cross-reactivity with rabbit muscle myosin (Dale et al, 1985, J. Exp. Med. 162:583) by ELISA.

EXAMPLE 6

Assays for M protein epitopes

The presence of protective M protein epitopes was determined by the inhibition of opsonization of type 6 streptococci by the synthetic peptides preincubated with opsonic antisera raised against S-M6(1–20), S-M6(10–20), and S-M6(12–31). The antisera (0.1 ml) were mixed with an equal volume of PBS containing 100 uM synthetic peptide. After incubation for 30 min at 37° C., the mixture was used in opsonophagocytosis tests of type 6 streptococci as described in Cunningham et al, 1975, J. Immunol. 115:1002. The values of the inhibition of opsonization were calculated as follows: [1-(percentage of neutrophils associated with streptococci in presence of inhibitor/percentage of neutrophils associated with streptococci in absence of inhibitor)]×100.

The invention also encompasses biologically active compositions comprising the antigen and an immunostimulant and wherein the antigen is administered with the immunostimulant. CFA is one such immunostimulant. Other natural and synthetic immunostimulants are well known in the art. The administration need not be concurrent; one may precede the other, in part of all of it. What is important is that the two components are present in the system of the mammal concurrently.

The biological compositions of the invention can be in any suitable form for administration to the mammal, whether a human or animal. Such are known in the art.

Solid compositions for oral administration include compressed tablets, pills, powders and granules. In such solid compositions, at least one of the active ingredients is admixed with at least one inert diluent such as starch, calcium carbonate, sucrose or lactose. These compositions may also contain additional substances other than inert diluents, e.g. lubricating agents, such as magnesium stearate, talc and the like.

Liquid compositions for oral administration include pharmaceutically-acceptable emulsions, solutions, suspensions, syrups and elixirs containing inert diluents commonly used in the art, such as water. According to the invention, the compounds for oral administration also include capsules of absorbable material, such as gelatin, containing said active component with or without the addition of diluents or excipients.

Preparation according to the invention for parenteral administration include sterile aqueous-organic, and organic solutions, suspensions and emulsions. Examples of organic solvents or suspending media are propylene glycol, polyethylene glycol, vegetable oils, such as ethyl oleate. These compositions can also contain adjuvants such as stabilising, preserving, wetting, emulsifying and dispersing agents. Aqueous compositions are by far preferred.

The percentage of active component in the said composition and method for causing the desired biological effect (e.g. immunological or hormonal inhibitory), can be varied so that a suitable dosage is obtained. The dosage administered to a particular patient is variable, depending upon the clinician's judgment using as the criteria: the route of administration, the duration of treatment, the size and condition of the patient, the potency of the active component, and the patient's response thereto. An effective dosage amount of active component can thus be determined best by the clinician considering all criteria and utilizing the best judgment on the patient's behalf. For practical considerations, the proportion may vary from about 0.01 to 20%, or higher, of active ingredient per composition. What is needed is that at least the minimum effective amount to give the desired effect be present.

The biological compositions of the invention can be used for vaccines to provide immunological protection against *Streptococcus pyogenes*.

Other aspects of the invention will readily become apparent to one skilled in the art.

TABLE I

Covalent structures of synthetic peptides of type 6 M protein

| Synthetic Peptide | Amino Acid Sequence |
|---|---|
| S-M6 (1-11) | |
| S-M6 (1-20) | RVFPRGTVENPDKARELLNK |
| S-M6 (10-20) | NPDKARELLNK |
| S-M6 (12-31) | DKARELLNKYDVENSMLQAN |
| S-M6 (22-31) | DVENSMLQAN |

TABLE II

Reactivity of synthetic peptides of type 6 M protein with rabbit antisera against whole type 6 streptococci

| Rabbit Serum | ELISA Titers Against | | | | |
|---|---|---|---|---|---|
| | Pep M6 | S-M6 (1-20) | S-M6 (10-20) | S-M6 (12-31) | S-M6 (22-31) |
| 1 | 102,400 | 12,800 | 12,800 | 400 | 200 |
| 2 | 102,400 | 25,600 | 51,200 | 800 | 100 |

TABLE III

Indirect opsonobacterial tests of rabbit antisera against synthetic peptides of type 6 M protein

| Rabbit Serum | Rabbit Number | Number of Colonies of Type 6 Streptococci after 3 hr. Growth in Test Mixture | |
|---|---|---|---|
| | | Inoculum 125 | Inoculum 34 |
| Normal Rabbit Serum | | 3440 | 1410 |
| Anti-pep M6 (control) | 7633 | 110 | 110 |
| Anti-S-M6(1-20) | 8413 | 10 | 0 |
| | 8414 | 40 | 30 |
| | 8415 | 220 | 90 |
| Anti-S-M6(12-31) | 8416 | 30 | 0 |
| | 8417 | 380 | 60 |
| | 8418 | 930 | 360 |
| Anti-S-M6(10-20) | 8429 | 1100 | 70 |

TABLE IV

Cross-reactivity by ELIZA of antisera raised against synthetic peptides of type 6 M protein with heterologous M serotypes

| Rabbit Serum | ELISA Antibody Titers Against | | | |
|---|---|---|---|---|
| | pep M6 | pep M5 | pep M19 | pep M24 |
| Anti-S-M6(1-20) | | | | |
| 8413 | 51,200 | 200 | 400 | 800 |
| 8414 | 12,800 | 100 | 100 | 100 |
| 8415 | 51,200 | 800 | 1,600 | 400 |
| Anti-S-M6(10-20) | | | | |
| 8428 | 200 | <100 | 100 | 100 |
| 8428 | 6,400 | 100 | 100 | 200 |
| 8430 | 800 | <100 | <100 | 100 |
| Anti-S-M6(12-31) | | | | |
| 8416 | 6,400 | 800 | 200 | 100 |
| 8417 | 3,200 | 200 | 200 | 100 |
| 8418 | 6,400 | 200 | 100 | 100 |
| Anti-S-M6(22-31) | | | | |
| 8461 | <200 | <200 | <200 | 200 |
| 8462 | <200 | <200 | <200 | 400 |
| 8463 | <200 | 200 | <200 | 200 |

TABLE V

Immunogolic cross-reacting among synthetic peptides of type 6 M protein

| Rabbit Antisera | Rabbit Number | ELISA Titer Against | | | | |
|---|---|---|---|---|---|---|
| | | S-M6 (1-20) | S-M6 (10-20) | S-M6 (12-31) | S-M6 (22-31) | pep M6 |
| Anti-S-M6(1-20) | 8413 | 102,400 | 51,200 | 200 | 3,200 | 51,200 |
| | 8414 | 5,200 | 6,400 | <200 | 200 | 12,800 |
| | 8415 | 102,400 | 12,800 | 200 | 800 | 51,200 |
| Anti-S-M6(10-20) | 8428 | 25,600 | 12,800 | <200 | 200 | 1,600 |
| | 8429 | 51,200 | 51,200 | 200 | 200 | 12,800 |
| | 8439 | 51,200 | 51,200 | 200 | 200 | 1,600 |
| Anti-S-M6(12-31) | 8416 | <200 | <200 | 51,200 | 200 | 6,400 |
| | 8417 | <200 | <200 | 12,800 | 400 | 3,200 |
| | 8418 | <200 | <200 | 12,800 | 400 | 6,400 |
| Anti-S-M6(22-31) | 8461 | <200 | <200 | 102,400 | 25,600 | <200 |
| | 8462 | <200 | <200 | 102,400 | 25,600 | <200 |
| | 8463 | <200 | <200 | 51,200 | 12,800 | <200 |

TABLE VI

Inhibition of opsonization by synthetic peptides of antisera raised against S-M6(1-20), S-M6(10-20), and S-M6(12-31)

| Rabbit Antiserum | Inhibitory Peptide* | Percent Inhibition of Opsonization of Type 6 Streptococcus |
|---|---|---|
| Anti-S-M6(1-20) (Rabbit 8413) | 1-20 | 100 |
| | 10-20 | 0 |
| | 12-31 | 0 |
| | 22-31 | 0 |
| | Pep M6 | 100 |
| Anti-S-M6(10-20) (Rabbit 8429) | 1-20 | 94 |
| | 10-20 | 97 |
| | 12-31 | 45 |
| | 22-31 | 0 |
| | Pep M6 | 94 |
| Anti-S-M6(12-31) (Rabbit 8416) | 1-20 | 10 |
| | 10-20 | 7 |
| | 12-31 | 100 |
| | 22-31 | 4 |
| | Pep M6 | 100 |

*Each peptide was tested at a concentration of 50 pM.

TABLE VII

ELISA Titer and Inhibition of Opsonization by S-M6(1-11) four weeks after injection in each of the three rabbits

| ELISA | % Inhibition of Opsonization |
|---|---|
| 6400 | 62 |
| 6400 | 10 |
| 3200 | 70 |

What is claimed is:

1. A synthetic polypeptide which comprises the amino acid sequence

X-Lys-Ala-Arg-Glu-Leu-Leu-Asn-Y wherein X is Asp, Asn-Pro-Asp or Arg-Val-Phe-Pro-Arg-Gly-Thr-Val-Glu-Asn-Pro-Asp
and Y is Lys or Lys-Tyr-Asp-Val-Glu-Asn-Ser-Met-Leu-Gln-Ala-Asn.

2. The synthetic polypeptide of claim 1 which has the amino acid sequence.
Arg-Val-Phe-Pro-Arg-Gly-Thr-Val-Glu-Asn-Pro-Asp-Lys-Ala-Arg-Glu-Leu-Leu-Asn-Lys.

3. The synthetic polypeptide of claim 1 which has the amino acid sequence
Asn-Pro-Asp-Lys-Ala-Arg-Glu-Leu-Leu-Asn-Lys.

4. The synthetic polypeptide of claim 1 which has the amino acid sequence
Asp-Lys-Ala-Arg-Glu-Leu-Leu-Asn-Lys-Tyr-Asp-Val-Glu-Asn-Ser-Met-Leu-Gln-Ala-Asn.

5. A synthetic antigen conjugate which comprises a polyvalent linkable carrier covalently linked to the polypeptide of claim 1 which antigen is able to elicit type M6 specific opsonic antibodies to Streptococcus pyogenes and which is not serologically cross-reactive with tissue antigens of the heart.

6. The synthetic antigen of claim 5 wherein the polyvalent linked carrier is a natural protein carrier.

7. The synthetic antigen of claim 6 wherein the carrier is tetanus toxoid.

8. An immunogenic biological composition which comprises a biologically acceptable diluent, an immunostimulant and in an amount sufficient to elicit opsonic antibodies to Streptococcus pyogenes and not be serologically cross-reactive with tissue antigens of the heart, the synthetic antigen of claim 5.

9. The immunogenic biological composition of claim 8 wherein the immunostimulant is complete Freund's adjuvant or a synthetic immunostimulant.

10. A method for controlling streptococcal infections in a mammal which comprises administering to a mammal in a dose sufficient to control Streptococcus pyogenes, the composition of claim 8, and controlling Streptococcus pyogenes in said mammal.

11. A synthetic polypeptide which comprises the amino acid sequence
Arg-Val-Phe-Pro-Arg-Gly-Thr-Val-Glu-Asn-Pro.

12. A synthetic antigen conjugate which comprises a polyvalent linkable carrier covalently linked to the polypeptide of claim 11 which antigen is able to elicit type M6 specific opsonic antibodies to Streptococcus pyogenes and which is not serologically cross-reactive with tissue antigens of the heart.

13. The synthetic antigen of claim 11 wherein the polyvalent linked carrier is a natural protein carrier.

14. The synthetic antigen of claim 11 wherein the carrier is keyhole limpet hemocyanin.

15. An immunogenic biological composition which comprises a biologically acceptable diluent, an immunostimulant and in an amount sufficient to elicit opsonic antibodies to Streptococcus pyogenes and not be serologically cross-reactive with tissue antigens of the heart, the synthetic antigen of claim 11.

16. A method for controlling streptococcal infections in a mammal which comprises administering to a mammal in a dose sufficient to control Streptococcus pyogenes, the composition of claim 15, and controlling Streptococcus pyogenes in said mammal.

17. A synthetic polypeptide which comprises the amino acid sequence.
Asp-Val-Glu-Asn-Ser-Met-Leu-Gln-Ala-Asn.

18. A synthetic antigen conjugate which comprises a polyvalent linkable carrier covalently linked to the polypeptide of claim 17 which antigen is able to evoke high titers of ELISA antibody against itself.

19. A vaccine which comprises a biologically acceptable diluent, an immunostimulant and in an amount sufficient to elicit opsonic antibodies to Streptococcus pyogene and not be serologically cross-reactive with tissue antigens of the heart, the synthetic antigen of claim 18.

20. A vaccine which comprises a biologically acceptable diluent, an immunostimulant and in an amount sufficient to elicit opsonic antibodies of Streptococcus pyogenes and not be serologically cross-reactive with tissue antigens of the heart, the synthetic antigen of claim 11.

21. A vaccine which comprises a biologically acceptable diluent, an immunostimulant and in an amount sufficient to elicit opsonic antibodies to Streptococcus pyogenes and not be serologically cross-reactive with tissue antigens of the heart, the synthetic antigen of claim 5.

* * * * *